US008942423B2

(12) United States Patent
Patwardhan et al.

(10) Patent No.: US 8,942,423 B2
(45) Date of Patent: *Jan. 27, 2015

(54) METHODS FOR AUTOMATIC SEGMENTATION AND TEMPORAL TRACKING

(71) Applicant: General Electric Company, Schenectady, NY (US)

(72) Inventors: Kedar Anil Patwardhan, Niskayuna, NY (US); Sandeep N. Gupta, Niskayuna, NY (US); David M. Mills, Niskayuna, NY (US); Aaron M. Dentinger, Niskayuna, NY (US); Yongjian Yu, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/910,620

(22) Filed: Jun. 5, 2013

(65) Prior Publication Data

US 2013/0267846 A1 Oct. 10, 2013

Related U.S. Application Data

(62) Division of application No. 12/645,781, filed on Dec. 23, 2009, now Pat. No. 8,483,432.

(51) Int. Cl.
*G06K 9/00* (2006.01)
*G06T 7/00* (2006.01)
(Continued)

(52) U.S. Cl.
CPC ............. *G06T 7/0012* (2013.01); *G06T 7/0089* (2013.01); *G06T 7/2046* (2013.01);
(Continued)

(58) Field of Classification Search
None
See application file for complete search history.

(56) References Cited

U.S. PATENT DOCUMENTS 6,251,072 B1 6/2001 Ladak et al.
6,322,509 B1 11/2001 Pan et al.
(Continued)

FOREIGN PATENT DOCUMENTS

CN 101393644 A 3/2009
EP 1152372 A2 11/2001
WO 2004/052016 A2 6/2004

OTHER PUBLICATIONS

Guerrero et al (Real-Time Vessel Segmentation and Tracking for Ultrasound Imaging Applications, IEEE Transactions on Medical Imaging, vol. 26, No. 8, Aug. 2007, pp. 1079-1090).*

(Continued)

*Primary Examiner* — Amara Abdi
(74) *Attorney, Agent, or Firm* — Andrus Intellectual Property Law, LLP

(57) ABSTRACT

In one embodiment, a method of detecting centerline of a vessel is provided. The method comprises steps of acquiring a 3D image volume, initializing a centerline, initializing a Kalman filter, predicting a next center point using the Kalman filter, checking validity of the prediction made using the Kalman filter, performing template matching, updating the Kalman filter based on the template matching and repeating the steps of predicting, checking, performing, and updating for a predetermined number of times. Methods of automatic vessel segmentation and temporal tracking of the segmented vessel is further described with reference to the method of detecting centerline.

7 Claims, 16 Drawing Sheets

(51) Int. Cl.
  *G06T 7/20* (2006.01)
  *A61B 8/08* (2006.01)
  *G06K 9/62* (2006.01)
  *G06K 9/34* (2006.01)
(52) U.S. Cl.
  CPC .............. *G06T 7/208* (2013.01); *A61B 8/0891* (2013.01); *A61B 8/483* (2013.01); *A61B 8/523* (2013.01); *G06T 2207/10136* (2013.01); *G06T 2207/20101* (2013.01); *G06T 2207/20116* (2013.01); *G06T 2207/30101* (2013.01)
  USPC ............ 382/103; 382/134; 382/173; 382/209

(56) References Cited

U.S. PATENT DOCUMENTS

| | | | |
|---|---|---|---|
| 6,385,332 | B1 | 5/2002 | Zahalka et al. |
| 6,464,641 | B1 | 10/2002 | Pan et al. |
| 7,043,290 | B2 | 5/2006 | Young et al. |
| 7,397,935 | B2 | 7/2008 | Kimmel et al. |
| 2005/0249399 | A1* | 11/2005 | Tek et al. ................. 382/154 |
| 2006/0159310 | A1* | 7/2006 | Boukerroui et al. ......... 382/107 |
| 2006/0251304 | A1* | 11/2006 | Florin et al. ............... 382/128 |
| 2008/0015440 | A1* | 1/2008 | Shandas et al. ............. 600/458 |
| 2008/0119736 | A1 | 5/2008 | Dentinger |
| 2009/0306507 | A1* | 12/2009 | Hyun et al. ................. 600/443 |
| 2010/0063398 | A1 | 3/2010 | Halmann |

OTHER PUBLICATIONS

Lee et al ("Automatic segmentation of 3D micro coronary vascular images", Medical image analysis, Oxford university press, Oxford, GB, vol. 11, No. 6, Oct. 27, 2007, pp. 630-647, XP022318287, ISSN: 1361-8415).*

Chutatape, O. et al., "Retinal Blood Vessel Detection and Tracking by Matched Gaussian and Kalman Filters" IEEE Engineering in Medicine and Biology Society, vol. 6, Oct. 29, 1998, pp. 3144-3149.

Cohen B. et al., "New Maximum Likelihood Motion Estimation Schemes for Noisy Ultrasound Images", Pattern Recognition, Elsevier, GB, XP004323385, ISSN: 0031-3203, vol. 35, No. 2, Feb. 1, 2002, pp. 455-463.

Hernades-Hoyos, Marcela et al., "Computer-assisted Analysis of Three-dimensional MR Angiograms", vol. 22, No. 2, Mar. 1, 2002, pp. 421-436.

Mansard C D, et al., "Quantification of Multicontrast Vascular MR Images with NL Snake, an Active Contour Model: In Vitro Validation and In Vivo Evaluation", Magnetic Resonance in Medicine, vol. 51, No. 2, Feb. 28, 2004, pp. 370-379.

Welch, et al., An Introduction to the Kalman Filter, UNC-Chapel Hill, TR 95-041, Jul. 24, 2006.

Noble, Ultrasound Image Segmentation: A Survey, IEEE Transactions on Medical Imaging, vol. 25, No. 8, Aug. 2006, p. 987-1010.

Guerrero, et al., Real-Time Vessel Segmentation and Tracking for Ultrasound Imaging Applications, IEEE Transactions on Medical Imaging, vol. 26, No. 8, Aug. 2007, p. 1079-1090.

Lee at al., "Automatic Segmentation of 3D Micro-CT Coronary Vascular Images", Medical Image Analysis, Oxford University Press, vol. 11, No. 6, Oct. 27, 2007, pp. 630-647.

Lesage. D, et al., "A Revim,v of 3D Vessel Lurnen Segmenlation Techniques: IVIodels, Features and Extraction Schemes" Medical Image Analysis, Oxford University Press, Oxford, GB, vol. 13, No. 6, Dec. 1, 2009, pp. 819-845.

Partial International Search Report from corresponding PCT Application No. PCT/US2010/059358, Apr. 29, 2011.

International Search Report and Written Opinion from corresponding PCT Application No. PCT/US2010/059358, Jun. 15, 2011.

Unofficial translation of SIPO Search Report from Chinese Patent Application No. 2010800646470 dated Apr. 22, 2014.

Cohen et al., "New Maximum Likelihood Motion Estimation Schemes for Noisy Ultrasound Images", Pattern Recognition, 2002, 35:455-463.

Guerrero et al., "Real-Time Vessel Segmentation and Tracking for Ultrasound Imaging Applications", IEEE Transations on Medical Imaging, Aug. 2007, 26(8):1079-1090.

Lee et al., "Automatic Segmentation of 3D micro-CT Coronary Vascular Images", Medical Image Analysis, 2007, 11 (6):630-647.

Lesage et al., "A Review of 3D Vessel Lumen Segmentation Techniques: Models, Features and Extraction Schemes", Medical Image Analysis, 2009, 13:819-845.

Matsuyama et al., "Developing Man-Machine Symbiotic Systems", Journal of Japanese Society for Artificial Intelligence, 2004, 19(2)1-10.

Nowinski et al., "A 3D Model of Human Cerebrovasculature Derived from 3T Magnetic Resonance Angiography", Neuroinform, 2009, 7:23-26.

Office Action for JP 2012-546000 dated Aug. 21, 2014.

* cited by examiner

METHODS FOR AUTOMATIC SEGMENTATION AND TEMPORAL TRACKING

CROSS-REFERENCE TO RELATED APPLICATIONS

This application is divisional of U.S. application Ser. No. 12/645,781, filed Dec. 23, 2009, which application was published on Jun. 23, 2011, as U.S. Publication No. 2011/0150274, the content of which are incorporated herein by reference in its entireties.

FIELD OF INVENTION

The invention relates in general to medical imaging, and more particularly to an improved segmentation and tracking method for real-time 3-dimensional ultrasound (real time 3-D US).

BACKGROUND OF THE INVENTION

Several medical procedures require placement of catheters inside a blood vessel of a human body. Placement of central catheters is currently performed blindly and then confirmed with X-ray after completion of the medical procedure. X-ray imaging has adequate resolution to see tiny vessels but also would cause radiation-related complications.

Toward improved and safer care for patients including fragile infants, real-time 3-D ultrasound imaging have been proposed to supplement or gradually replace current X-ray imagers to help clinicians in performing catheter insertion operation.

The real-time and radiation-free imaging capabilities of ultrasound make it a more appealing option than X-ray-based imagers for guiding interventional procedures. Further, usage of ultrasound images in real-time, may facilitate carrying out the medical procedure in many ways, including improved outcomes for the infants and quicker completion of the medical procedures. However, ultrasound image suffers from heavy speckle noise and lower spatial resolution. It is challenging for a clinician to visualize and follow the moving blood vessels in the raw, real-time images when both hands are occupied wherein one hand holds and sweeps the probe; and the other handles the catheter delicately. According to clinical literature, improper positioning of central catheters is a suspected cause of severe complications that may lead to death of fragile patients.

On the other hand, when performing diagnostic procedures, medical personnel that perform these procedures are not trained in the use of ultrasound and thus are not used to the images procured by medical ultrasound systems. Several methods have been proposed in the prior art describing was in which ultrasound-imaging methods can be used to enhance visualization.

Some of the limitations as with the prior art methods include, low image quality and signal to noise ratio, large motion of vessel of interest, small size of the vessel of interest, disappearance of portions of the vessel due to artifacts etc, clutter in the data due to presence of other structures and/or vessels in the vicinity of the vessel of interest, high temporal frame rate of data and the need for segmentation and tracking to match the data acquisition speed.

In particular, one of the prior art method describes an algorithm for segmenting a vessel cross section in a single 2D slice, and then tracking the segmented vessel in single 3D volume. This method does not address the temporal tracking aspect, i.e., the method does not describe updating the vessel segmentation over time to account for motion.

Several approaches for vessel segmentation or tubular structure segmentation have been proposed for other imaging modalities. However, the methods are not applicable to ultrasound data and temporal tracking applications.

Hence there exists a need for a method for tracking blood vessels that is simple, provides time efficient tracking of blood vessels that is easy to visualize and comprehend, robust in complex environments and computationally efficient.

BRIEF DESCRIPTION OF THE INVENTION

The above-mentioned shortcomings, disadvantages and problems are addressed herein which will be understood by reading and understanding the following specification.

In one embodiment, a method of detecting centerline of a vessel is provided. The method comprises steps of acquiring a 3D image volume, initializing a centerline, initializing a Kalman fiber, predicting a next center point using the Kalman filter, checking validity of the prediction made, performing template matching based centerline detection for estimating measurement error, updating the Kalman filter based on the template matching and repeating the steps of predicting, checking, performing and updating until the end of the vessel or for a predetermined number of times.

In another embodiment, an automated segmentation method for generating a surface contour of a vessel is provided. The method comprises steps of initializing a vessel cross section, initializing an iteration counter, evolving an active contour towards a vessel boundary, regularizing a contour from the active contour evolution by using least square fining, determining if the value of the iteration counter is greater than a predetermined value, performing re initialization using the regularized contour if the value of the iteration counter is less than the predetermined value, incrementing the iteration counter and repeating the steps of evolving, regularizing, determining, performing and incrementing until the entire vessel has been segmented.

In yet another embodiment, a method of segmenting a vessel comprising a plurality of cross sections is provided. The method comprises steps of acquiring a 3D image volume, initializing, one or more Kalman filter parameters using a preset configuration file, selecting an initial center point within the vessel to be segmented, performing an initial segmentation on a first image slice based on the initial center point, the first image slice being a 2D cross-section of the vessel, creating a template of a vessel cross section based on the initial segmentation, predicting a next center point that is a translation of the initial center point along a beam direction using the Kalman correcting the next center point based on a measurement of the next center point in the image volume, segmenting a second image slice based on the next center point and repeating the steps of predicting, correcting and segmenting until the vessel has been completely segmented in the 3D image volume.

In another embodiment, a method of vessel temporal tracking is provided. The method comprises steps of: acquiring a 3D image volume, initializing one or more Kalman fitter parameters using a preset configuration file, identifying a first image slice, performing an initial segmentation on the first image slice, selecting an initial center point of the segmented image slice, creating a template of a vessel cross section around the initial center point based on the initial segmentation, the template being an elliptical model, finding a next center point by the steps of: copying parameters of the adapted elliptical model to a plurality of candidate points neighboring the initial center point, orienting an elliptical adaptable model around each of the plurality of candidate points using the copied parameters searching for center points around each of the candidate points based on the elliptical adapted model wound each of the candidate points, adapting the elliptical adaptable models around the candidate points to the found center points, selecting one of the candidate points whose adapted model fits best to the vessel as the next center point and repeating the step of finding a next center point until an end point of the vessel centerline or a predetermined number of iterations are reached.

In yet another embodiment, a computer system comprising: a processor and a program storage device readable by the computer system, embodying a program of instructions executable by the processor to perform method steps for automatic segmentation and temporal tracking of a blood vessel in a 2D or 3D image data set by extracting a centerline along the Wood vessel in a selected region is provided. The method comprises steps of acquiring an image volume from an ultrasound imaging system, performing vessel segmentation on the 3D image volume to generate a 3D ultrasound image of the blood vessel, detecting a vessel centerline for the segmented blood vessel, estimating cross-sectional area of the segmented blood vessel using the detected vessel centerline and performing temporal tracking of the estimated cross-section based on template matching.

Systems and methods of varying scope are described herein. In addition to the aspects and advantages described in this summary, further aspects and advantages will become apparent by reference to the drawings and with reference to the detailed description that follows.

DETAILED DESCRIPTION OF INVENTION

Figure 1:
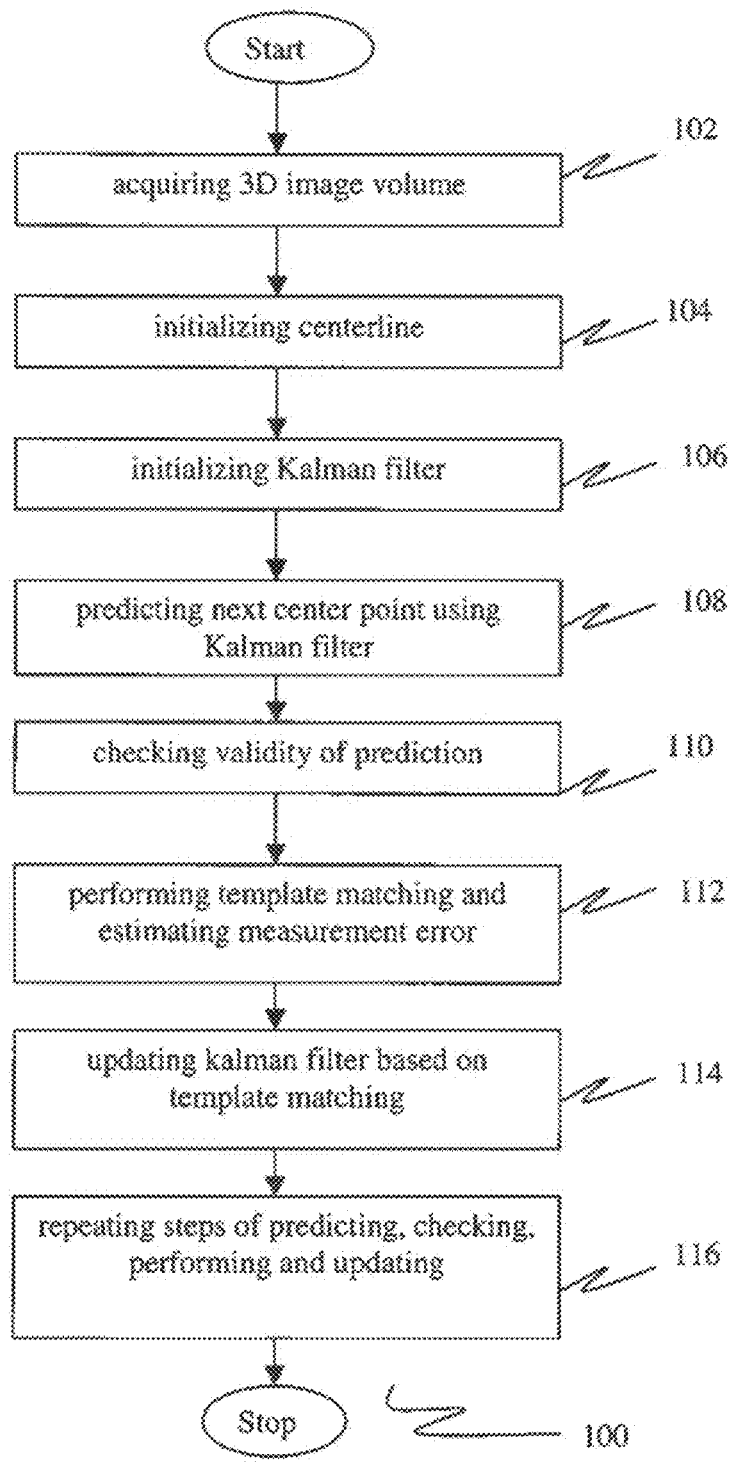
FIG. 1 shows a flowchart that describes an over-view of a template-matching based vessel-centerline detection method described in one embodiment.

In the following detailed description, reference is made to the accompanying drawings that form as part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Ultrasound is a widely used medical imaging modality. It is inexpensive, widely accessible, fast, and safe. Ultrasound image to is required in a number of medical examinations. For example, obstetrics, in measuring dimensions of various anatomical features of the fetus; in oncology, for outlining the prostate for radiation treatment planning; in cardiovascular applications, for diagnosing deep venous thrombosis (DVT) and atherosclerosis using segmented features in ultrasound images.

Premium medical diagnostic ultrasound imaging systems require a comprehensive set of imaging modes. These are the major imaging modes used in clinical diagnosis and include timeline Doppler, color flow Doppler, B mode and M mode. In the B mode, such ultrasound imaging systems create two-dimensional images of tissue in which the brightness of a pixel is based on the intensity of the echo return. Alternatively, in a color flow imaging mode, the movement of fluid (e.g., blood) or tissue can be imaged. Measurement of blood flow in the heart and vessels using the Doppler effect is well known. The phase shift of backscattered ultrasound waves may be used to measure the velocity of the backscatters from tissue or blood. The Doppler shift may be displayed using different colors to represent speed and direction of flow. In the spectral Doppler imaging mode, the power spectrum of these Doppler frequency shifts are computed for visual display as velocity-time waveforms.

In ultrasound imaging, it is useful to segment blood vessels for visualization and for aiding and guiding procedures such as catheter placement etc. Often volumetric data is collected over time, where it may be important to maintain the correct segmentation by updating the segmentation of the vessel of interest as it moves due to physiological or probe motion. The invention relates to ultrasound segmentation methods, a broad sense, focusing on techniques developed for medical B-mode ultrasound images.

The vessel is selected from the group consisting of blood, lymph and lacteal. The vessel can be characterized based the position of the vessel center, the local orientation of the vessel, a model of the vessel cross-section, and the intensity distribution of the vessel's voxels.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. The methods of the inventions ate not limited to such images, and can be applied to images of any dimension, e.g. a 2-D picture or a 3-D volume.

In particular, the invention provides methods for performing real time segmentation and temporal tracking of a vessel of interest from volumetric ultrasound image data. The segmentation consists of two parts: (1) First detecting the centerline of the vessel; and (2) Estimating the boundary of the vessel (or a mask of the vessel) on a set of 2-D image slices that are uniformly spaced along the vessel alignment direction. The vessel alignment direction is assumed to be parallel to beam direction. This segmentation method could be applied to each temporal frame to get a new, segmentation of the vessel in presence of motion.

The cross-section estimation method described herein is based on active contours (or snakes). Active contours can be divided into two classes: the edge based relying on the image gradient to attract the snakes; and the region based that depend on region based statistical features. Region based active contours excel over the edge based wherever clutter and noise precludes movement of the edge based contour. Furthermore, region based contours are much less sensitive to the initialization of the contour than the edge based. To ensure robustness, a region based active contour segmentation method is adopted which is driven by mean-difference binary flows. Active contours are computed using either level set or parametric method. The former allows possible topological changes of curves, but is expensive in terms of computational cost. For real-time performance, the parametric method can be chosen to implement active contours in the cross-section estimation method.

Alternatively, the invention proposes a temporal tracking method, in which one or more selected parameters of the vessel segmentation in chosen temporal frames can be updated. The segmentation result can then be used to improve the visualization of the vessel of interest and guide subsequent imaging and procedures. This yields a real-time implementation of vessel segmentation and tracking.

Accordingly, in one embodiment, the invention describes a method used for the initial detection of a vessel-centerline in a first B-mode ultrasound volume. The vessel centerline detection is important because it provides guidance for a physician for inserting a catheter through the vessel. Further, vessel centerline detection is vital in the visualization of the vessel (for clinical use) as the subsequent visualization steps (vessel cross-section estimation, temporal vessel tracking, catheter detection, etc) depend heavily on the accurate and robust detection of the vessel-centerline. In this method an assumption is made that the vessel lies along one of the main co-ordinate ages (beam direction). Based on this assumption, the method performs 2D template based vessel centerline detection.

FIG. 1 shows a flowchart that describes an over-view of the template-matching based vessel-centerline detection method 100. The method 100 comprises steps of acquiring a 3D image volume at step 102, initializing a centerline at step 104, initializing a Kalman filter at step 106, predicting a next center point using the Kalman filter at step 108, checking validity of the prediction made using the Kalman filter at step 110, performing template matching at step 112, updating the Kalman filter based on the template matching at step 114 and repeating the steps of predicting, checking, performing and updating for a predetermined number of times at step 116.

Figure 2:
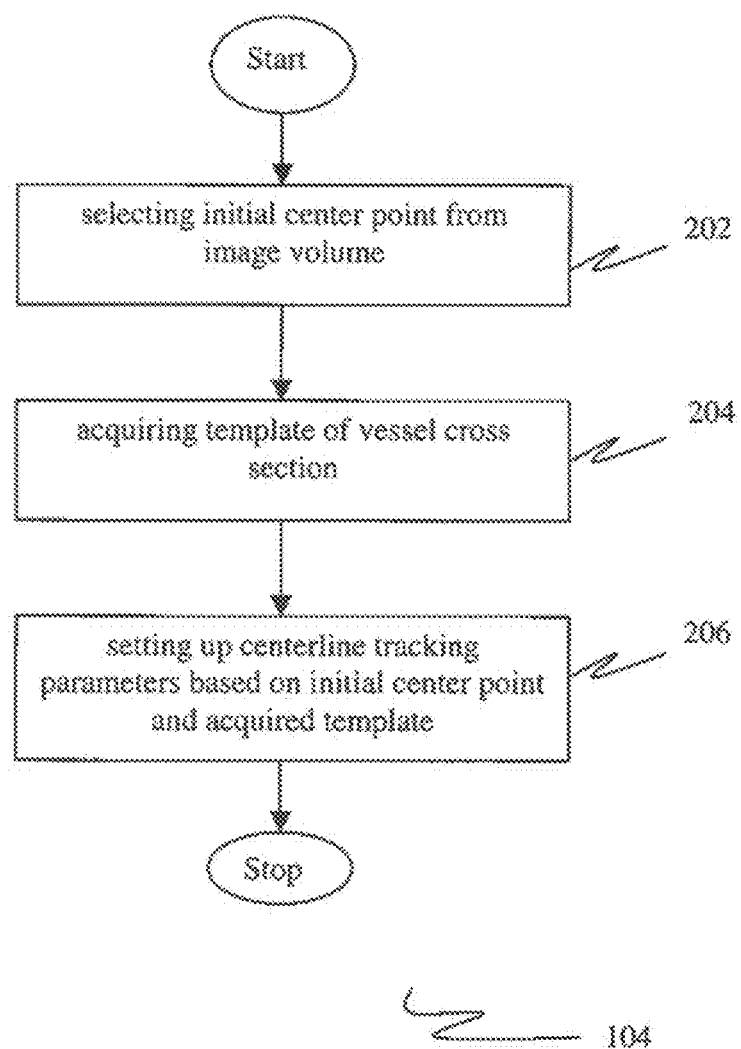
FIG. 2 shows a flow chart that &scribes the step of initializing a centerline, shown in FIG. 1.

The step 104 of initializing a centerline is described in FIG. 2. With reference to FIG. 2, step 104 comprises selecting an initial center point from the image volume at step 202, acquiring a template of a vessel cross section at step 204 and setting up centerline tracking parameters based on the initial center point and the acquired template at step 206.

An initial center point is selected from the 3D image volume obtained from the ultrasound imaging system. The initial center point thus identified is also referred to as a seed point. Given an initial seed point, a Kalman filter that use 2D template matching is employed. Kalman filters are used for tracking the seed point in real-time ultrasound images. The movement of the seed point through space is described by a dynamic model and measurements are used to estimate the position of the seed point.

Figure 3:
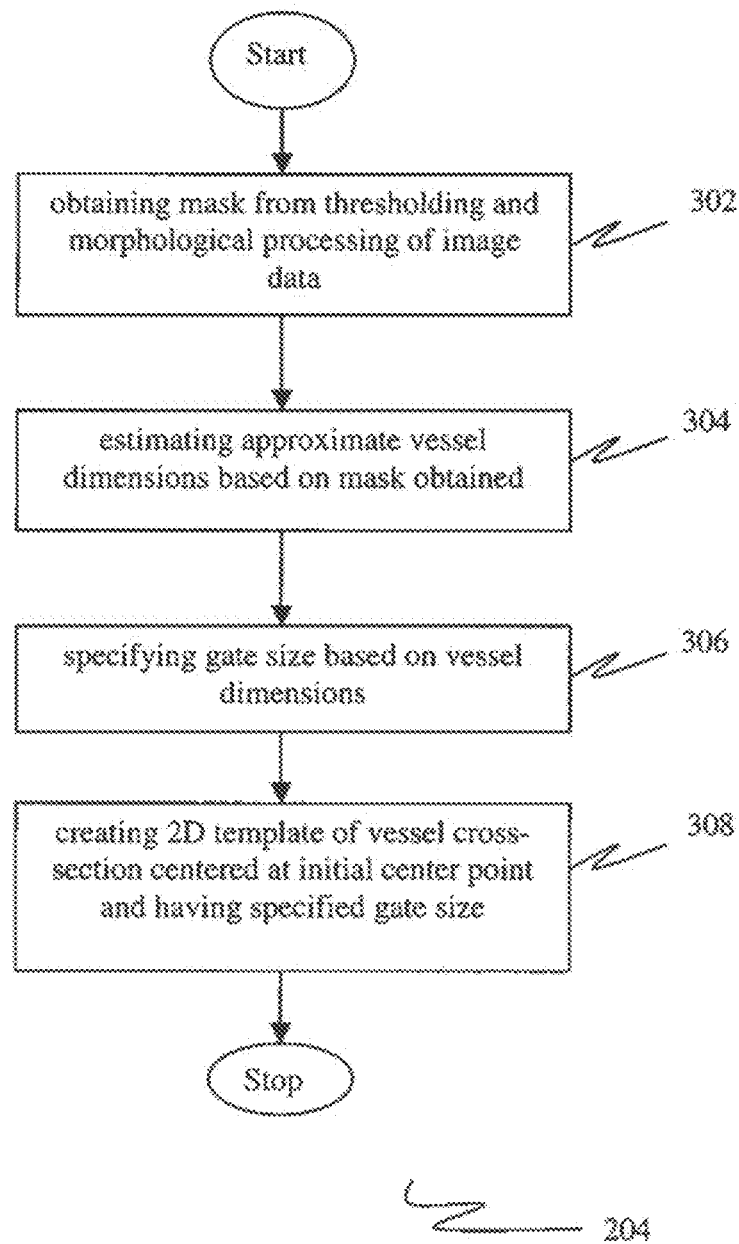
FIG. 3 shows as flow chart that describes the step of, acquiring vessel template, shown in FIG. 2.

The step 204 of acquiring template of vessel cross-section is further explained in conjunction with FIG. 3. With reference to FIG. 3, step 204 comprises steps of obtaining a mask from thresholding and morphological processing of image data step 302, estimating approximate vessel dimensions based on the mask obtained step 304, specifying a gate size based on the vessel dimensions; step 306 and creating a 2D template of the vessel cross-section centered at the initial center point and having the specified gate size step 308.

The 2D image-patch around the initial-seed point as used for initializing the template that is used for detecting, the vessel cross-se non in subsequent slices. Further, the mask from thresholding and morphological processing of the image data above is used to estimate the approximate vessel dimensions.

These vessel dimensions help in specifying the template size (this is also referred to as "gate-size"). Subsequent to the detection of the initial seed point and the template initialization, a 2D template of the vessel cross-section centered at the initial seed point is created.

Referring back to FIG. 2, initializing a centerline at step 104 further comprises step 206 of setting up centerline tracking parameters. The parameters for the centerline tracking are of two types: Kalman filter parameters and template matching parameters, Kalman filter parameters include process noise variance (Q), measurement error variance (R), prediction error variance (also referred to as estimation error variance) (P), Kalman Gain (K), Delta_T (time-step) and Lambda (parameter that is used to update the measurement error variance).

Template matching parameters include initial observation window size, motion-direction (desired motion along a selected dimension in the 3D volume), match score threshold and alpha, parameter that controls match-score computation (holds the ability to bias the template matching results in favor of the candidate that is closer to the prediction).

The Kalman filter estimates a process by using a form of feedback control: the filter estimates the process state at some time and then obtains feedback in the form of (noisy) measurements. As such, the equations for the Kalman filter fall into two groups: time update equations and measurement update equations. The time update equations are responsible for projecting forward (in time) the current state and error variance estimates to obtain the priori estimates for the next time step. The measurement update equations are responsible for the feedback—i.e. for incorporating a new measurement into the a priori estimate to obtain an improved posteriori estimate. The time update equations can also be thought of as predictor equations, while the measurement update equations can be thought of as corrector equations. The final estimation method resembles that of a predictor-corrector method for solving numerical problems.

Referring back to FIG. 1, the method 100 at step 106 comprises initializing the Kalman filter. For initializing the Kalman filter the Kalman filter parameters listed above are obtained from a preset configuration file. In subsequent timesteps, they get updated and are used for the subsequent timesteps.

The method 100 further comprises predicting a next center point using the Kalman filter at step 108. Step 108 is further explained in conjunction with FIG. 4. Using the Kalman filter to predict a next center point comprises defining a transition matrix for translating the initial center point by a spatial displacement along the beam direction, defining is prediction error variance P for the initial center point, predicting a next center point and a next prediction error variance based on the transition matrix, defining process noise variance for the prediction error variance and the series of center point measurements, correcting the center point prediction based on a measurement error variance, a measurement of the predicted center point, and the process noise variance of the center point measurements, and correcting the prediction error variance based on the measurement error variance and the process noise variance of the center point measurements.

Figure 4:
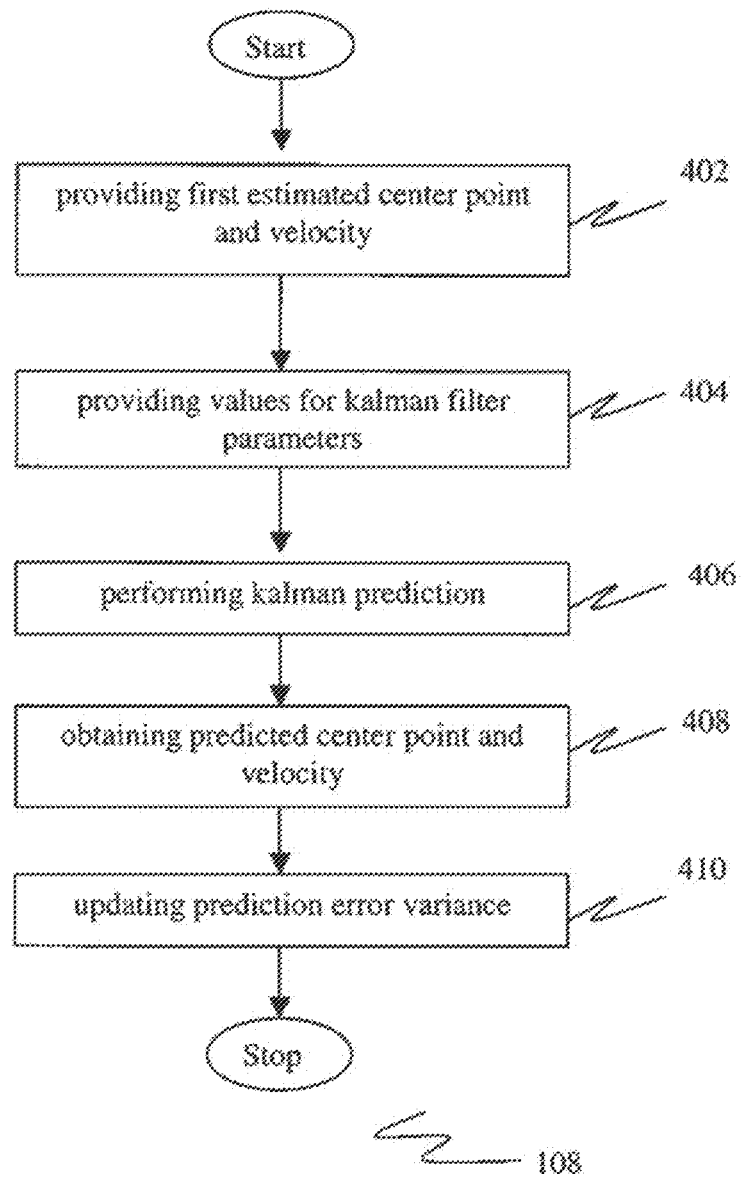
FIG. 4 shows a flow chart that describes the process of predicting a next center point, shown as a step in FIG. 1.

Accordingly, with reference to FIG. 4, step 108 comprises providing a first estimated center point and velocity at step 402, providing values for Kalman filter parameters at step 404, performing Kalman prediction at step 406, obtaining a predicted center point and velocity at step 408 and updating prediction error variance at step 410.

In the Kalman filter, the time update projects the current state estimate ahead in time. The measurement update adjusts the projected estimate by an actual measurement at that time. The time update equations project the state and variance estimates forward from time step k-1 to step k. Accordingly, first estimated center and velocity could also be equated to be last estimated center and velocity, represented by $C_{k-1}$ and $V_{k-1}$ respectively. However, for a first iteration, the first estimated center point is the initial center point or the seed point and the velocity is approximated to be a constant. The outputs obtained from the Kalman filter prediction are predicted center ($C_{kp}$) and velocity ($V_{kp}$) and updated prediction/estimation error variance $P_k$.

The method 100 further comprises step 110 for checking validity of the prediction made using the Kalman filter at step 108. This step 110 checks if the predicted Center ($C_{kp}$) is within the volume bounds, and also that the estimation error is reasonable. Accordingly, step 110 comprises checking if the predicted center point lies within a predetermined volume such as the acquired template and checking if the prediction error variance is below an estimation threshold. The estimation threshold can be obtained from earlier detections.

Subsequent to checking the validity of prediction made using the Kalman filter at step 110, the method 100 further comprises performing template matching at step 112. The template matching is performed between the next center point estimated and measured center point measured using the Kalman filter. When tracking features in ultrasound images over several frames, template matching is a common procedure; the feature to be detected is described by a mask and a correlation procedure is performed to determine its location.

Figure 5:
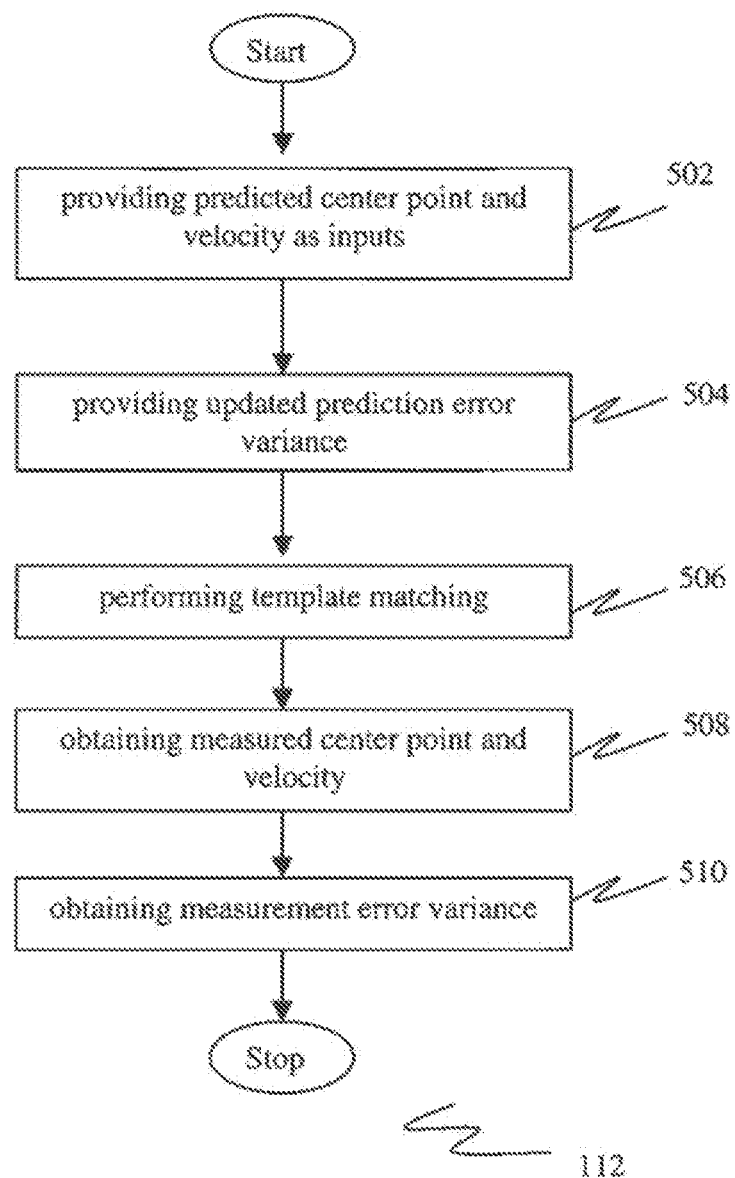
FIG. 5 shows a flow chart that describes performing template matching described as a step in FIG. 1.

Step 112 of performing template matching is f ether explained in conjunction with FIG. 5. With reference to FIG. 5, step 112 comprises steps of providing the predicted center point and velocity as inputs at step 502, providing updated prediction error variance at step 504, performing template matching at step 506, obtaining a measured center point and velocity at step 508 and obtaining measurement error variance at step 510. In one embodiment, the template matching is performed based on Rayleigh approximation of speckle noise distribution. Rayleigh approximation is well known to those skilled in the art and hence will not be described in detail.

The inputs provided to the Kalman filter for performing template matching are predicted center ($C_{kp}$), velocity ($V_{kp}$) and prediciton/estimation error variance $P_k$ obtained from the prediction step 108. A feedback is provided using measurement update equations for incorporating a new measurement into the a priori estimate to obtain an improved posteriori estimate. Accordingly, the outputs obtained subsequent to performing template matching at step 112 are measured center ($C_{km}$) and velocity ($V_{km}$) and measurement error variance ($R_k$).

Figure 6:
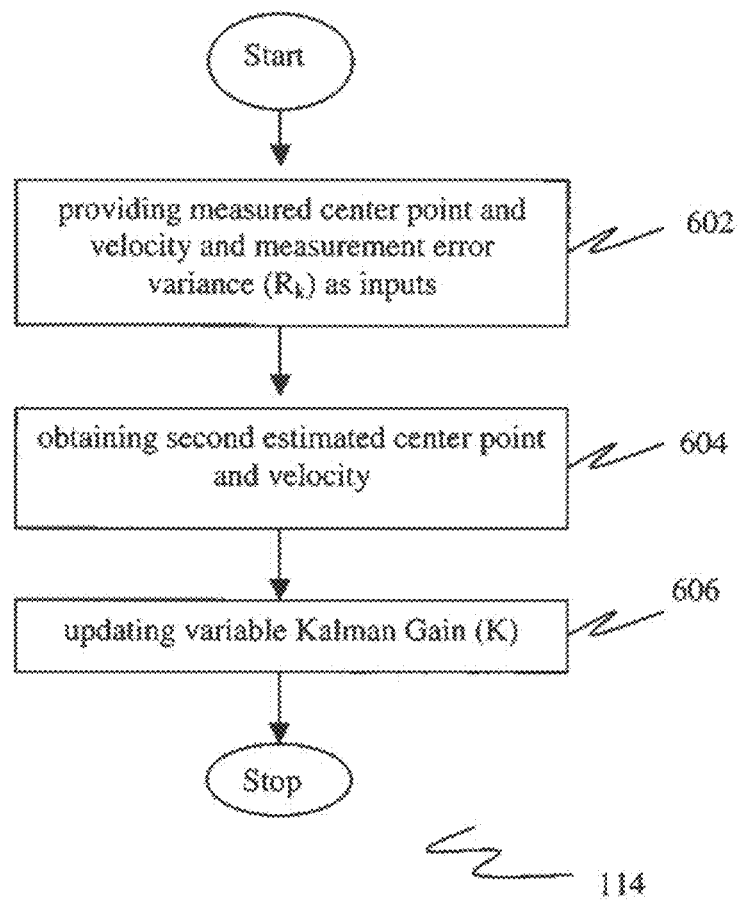
FIG. 6 shows a flow chart that describes the step of updating the Kalman filter shown in FIG. 1.

A measurement update at step 114 is carried out following the step 112 as depicted in FIG. 1. Step 114 is further explained in conjunction with FIG. 6. With reference to FIG. 6, step 114 comprises steps of providing the measured center point and velocity and measurement error variance ($R_k$) as inputs at step 602, obtaining a second estimated center point and velocity at step 604 and updating the variable Kalman Gain (K) at step 606.

In the Kalman filter update step 114, measured center ($C_{km}$) and velocity ($V_{km}$) and measurement error variance ($R_k$) obtained as outputs at step 112 are fed as inputs. A second estimated center ($C_k$) and velocity ($V_k$) are obtained as outputs. As can be understood by those skilled in the art, the second estimated center ($C_k$) is also the next center point.

The first task during the measurement update is to compute the Kalman gain. The next step is to actually measure the process, and then to generate a posteriori estimate by incorporating the measurement. The final step is to obtain a posteriori error variance estimate. The Kalman gain (K) thus obtained is updated thereafter for use in the future iterations.

After each time and measurement update pair, the process is repeated with the previous posteriori estimates used to project or predict the new priori estimates. Accordingly, the method 100 comprises repeating the steps of predicting, checking, performing and updating for a predetermined number of times at step 116. The predetermined number can be selected based on the iterations required for reaching the end of the vessel. This recursive nature is one of the very appealing features of the Kalman filter as it makes practical implementations much more feasible.

Figure 7A:
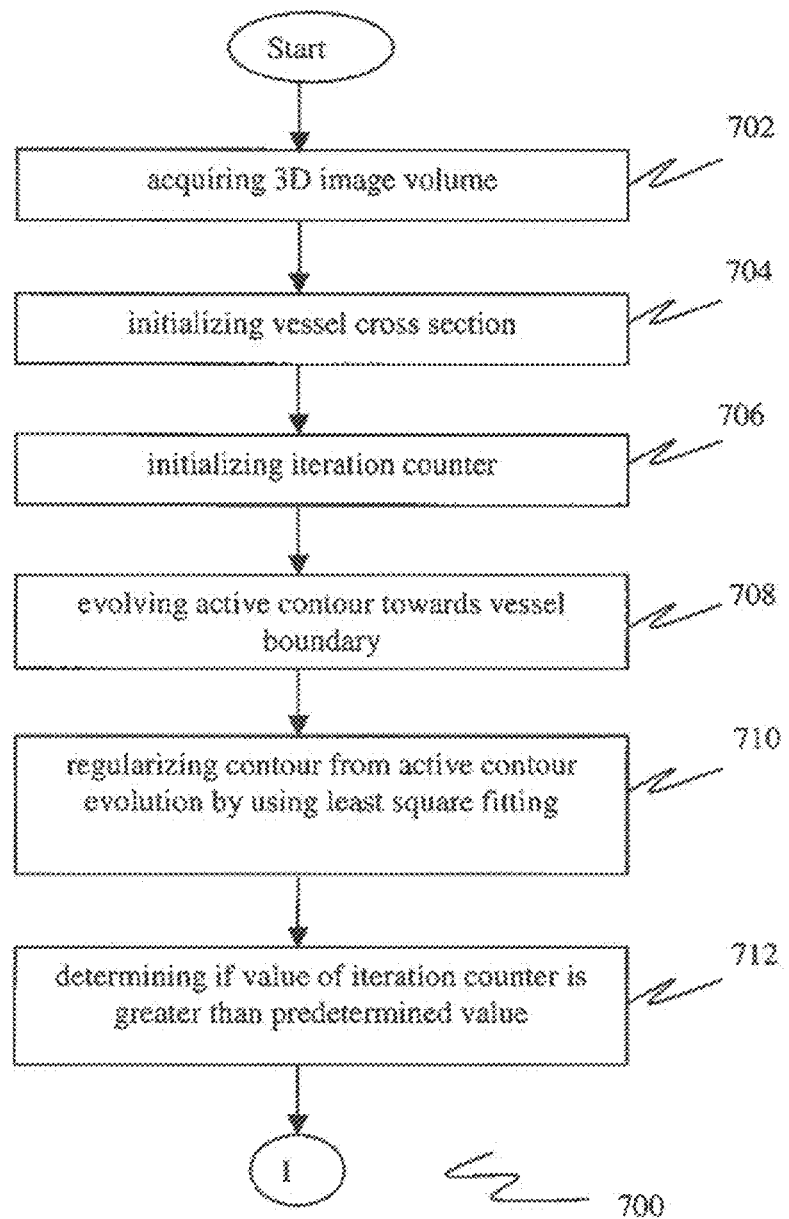
FIG. 7A and FIG. 7B show a flow chart that describes an automated segmentation method for generating a surface contour described in one embodiment.
Figure 7B:
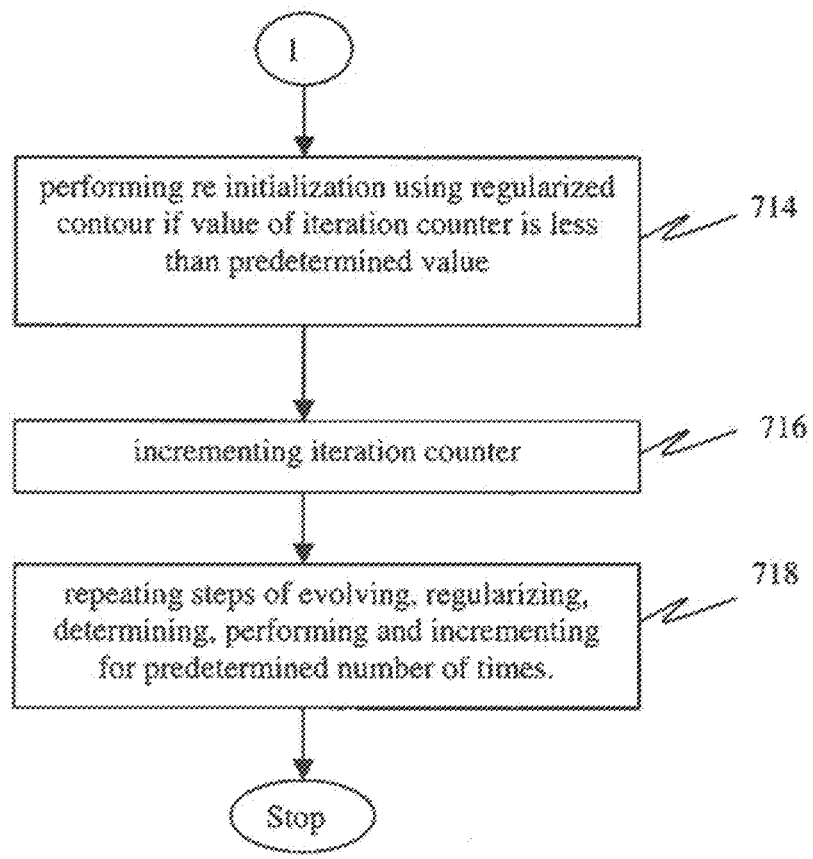

In another embodiment, as shown in FIG. 7A and FIG. 7B, an automated segmentation method 700 for generating a surface contour of the vessel is provided. The vessel segmentation uses an extended Kalman filter and an elliptical vessel model to determine the vessel boundary and estimate ellipse parameters for that vessel, which can be used to quickly calculate the transverse area.

The method 700 comprises steps of acquiring a 3-D image volume at step 702, initializing a vessel cross section at step 704, initializing an iteration counter at step 706, evolving an active contour towards a vessel boundary at step 708, regularizing a contour from the active contour evolution by using least square fitting at step 710, determining if the value of the iteration counter is greater than a predetermined value at step 712, performing re initialization using the regularized contour if the value of the iteration counter is less than the predetermined value at step 714, incrementing the iteration counter at step 716 and repeating the steps of evolving, regularizing, determining, performing and incrementing for a predetermined number of iterations indicated by the predetermined value at step 718.

The vessel cross-section segmentation method 700 is developed to automatically delineate the boundaries of the vessels of interest from 3D imagery and the estimated vessel centerlines. The boundary of a vessel is drawn as a sequence of closed planar curves in a set of parallel image planes uniformly distributed along the alignment direction of the vessel.

Figure 8:
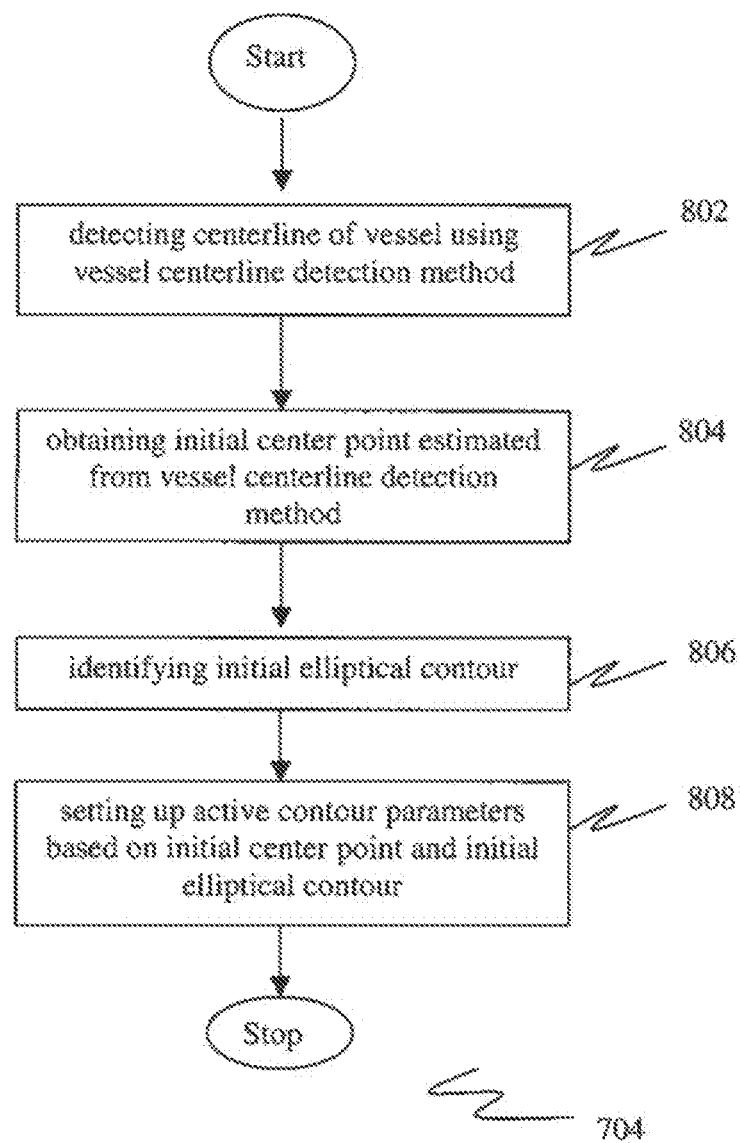
FIG. 8 shows a flow chart that describes the initializing step shown in FIG. 7.

Step 704 of initializing is further explained in conjunction with FIG. 8. With reference to FIG. 8, step 704 comprises detecting centerline of a vessel using the vessel centerline detection method 100 at step 802, obtaining an initial center point estimated from the vessel centerline detection method 100 at step 804, identifying an initial elliptical contour at step 806 and setting up active contour parameters based on the initial center point and the initial elliptical contour at step 808.

Figure 9:
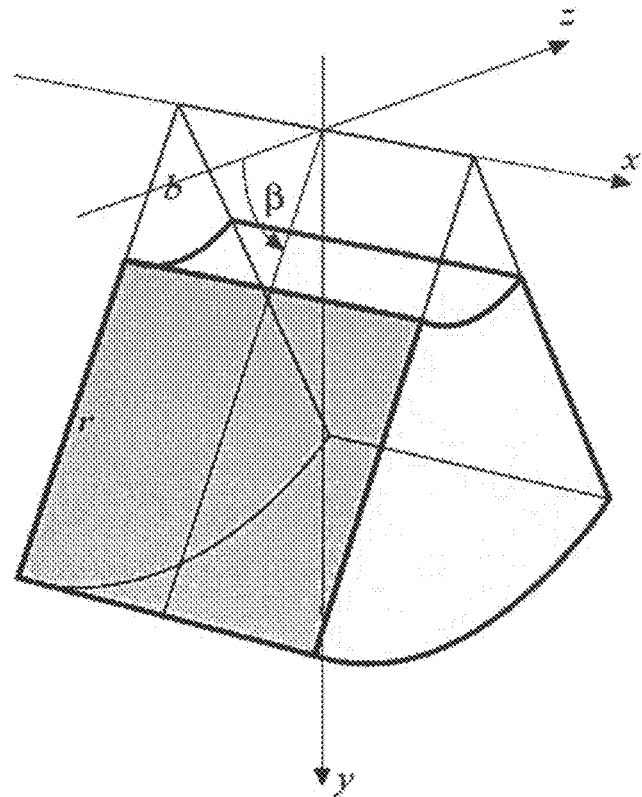
FIG. 9 illustrates a 3D imaging geometry and the coordinate systems corresponding to sweeping a linear array in elevation direction.

FIG. 9 illustrates a 3D imaging geometry and the coordinate systems corresponding to sweeping a linear array in elevation direction. The vessel of interest is aligned along the x-axis. It is conveniently assumed that in any 2-D image slice, parallel to the (z, y) plane, the vessel cross-section appears in general as a convex region with an approximately elliptical shaped boundary. The boundary can be represented by three geometric parameters: the lengths of the major and minor axes and the orientation of the major axis measured from a reference axis such as the z-axis (or column axis).

Figure 10:
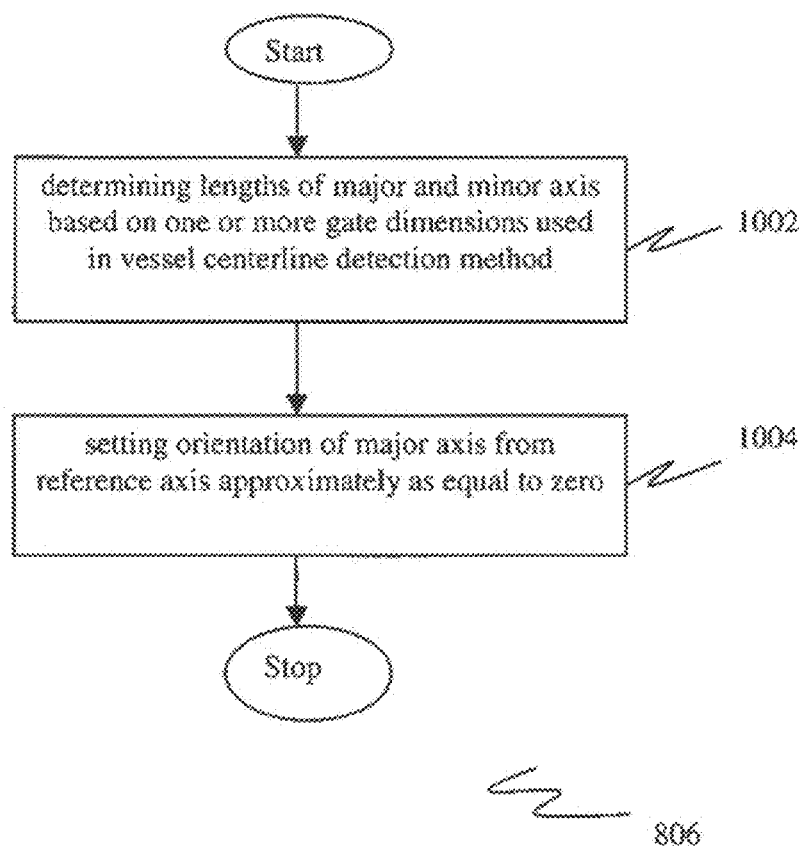
FIG. 10 shows a flow chart that describes the step of identifying initial elliptical contour shown in FIG. 8.

Step 806 of identifying initial elliptical contour is further explained in conjunction with FIG. 10. With reference to FIG. 10, step 806 comprises steps of determining lengths of the major (z-axis) and the minor axis (y-axis) based on the gate dimensions used in the vessel centerline detection method 100, at step 1002 and setting the orientation of the major axis from a reference axis (z-axis in this exemplary embodiment) approximately as equal to zero at step 1004.

Subsequent to identifying the initial elliptical contour at step 806, the method 704 of initializing the vessel cross-section further comprises setting up active contour parameters shown as step 808. The parameters for the segmentation and tracking are selected automatically based on expected vessel size and depth. Step 808 of setting up active contour parameters comprises specifying one or more active contour parameters. The one or more active contour parameters comprise weight parameters for area weighted mean difference, weight parameter for curve length, time step size for curve evolution, maximum re-iteration value and tolerance of contour convergence.

Active contour or snake approach is utilized to extract the curve outlining the cross-sectional boundary of a vessel in any image plane. As the cross-sections of vessels resemble ellipses in general, the permissible boundary curves ate restricted to elliptical shape by least squared error fitting. Combining the detected centerline and estimated cross-sections makes a complete and compact vessel model that not only eases a clinician's difficulty to correctly and precisely place and advance the catheter, but also allows forming clinically significant views of the catheter going through real-time 3D data.

The cross-section estimation procedure is performed by consecutively traversing the contour several times, typically three. The original seed point is used throughout, and a new seed point is not calculated until the next image is processed. The extracted contour and the reconstructed ellipse are compared to each other, at additional computational expense, to insure smoothness for the contour. The root mean squared (rms) radial distance between boundaries is used as an error measure, and is computed by measuring the distance between the estimated points and the corresponding points on the generated ellipse. A data fit is deemed invalid if this error is larger than a threshold.

An iteration counter is employed to keep track of the iterations involved in evolving an active contour towards the vessel boundary. As can be seen from FIG. 7, the iteration counter is initialized at step 706. Accordingly, the method 700 further comprises the step of evolving the initial elliptical curve toward the vessel boundary at step 708.

In one embodiment, given an initial sample, a number of likely modes are first determined or refined from an image using a conventional "active contour technique" by performing an iterative search a 2D image plane. Conventional active contour techniques provide a deformable curve, or "snake", which moves over an image while minimizing its potential energy. The energy of a snake can in general be divided into an "internal energy" term constraining the overall shape of the snake, and an "external energy" function provided by the image driving the snake towards a desired boundary. With an appropriate image energy function and careful initialization, an active contour snake can converge effectively to the required boundary, thereby generating one or more modes. Such conventional active contour techniques are well known to those skilled in the art, and will not be discussed in further detail.

Inputs for the step 708 for evolving the initial elliptical curve towards the vessel boundary comprise the initial center point detected by the vessel centerline detection method 100, centerline of the vessel structure detected from the method 100, initial elliptical contour obtained from step 806 and active contour parameters. Output of the vessel cross-section estimation provides an N×5 array with each row representing the vessel center position (row and column indices) and cross section ellipse parameters (a, b, θ). The unit of θ is radian. N is the number of centerline points. The slice index is not stored in the cross-section segmentation list as it is already contained in the centerline list. It can be easily derived by using the slice-step parameter.

The method 700 further comprises regularizing a contour from the active contour evolution by using least square fitting of an ellipse to the contour points at step 710. Inputs for ellipse fitting performed at step 710 include a set of 2D points' coordinates (rows, cols). The returned vector contains the center, radii, and orientation of the ellipse, stored as (Cx, Cy, Rx, Ry, theta). Theta is in radian unit. Thereby an initial segmentation of the 3D image volume is performed. The resulting curve may not necessarily be an ellipse. However, estimated ellipse parameters and the final search area from one image are used to initialize the contour detection in the following image frame.

Figure 11A:
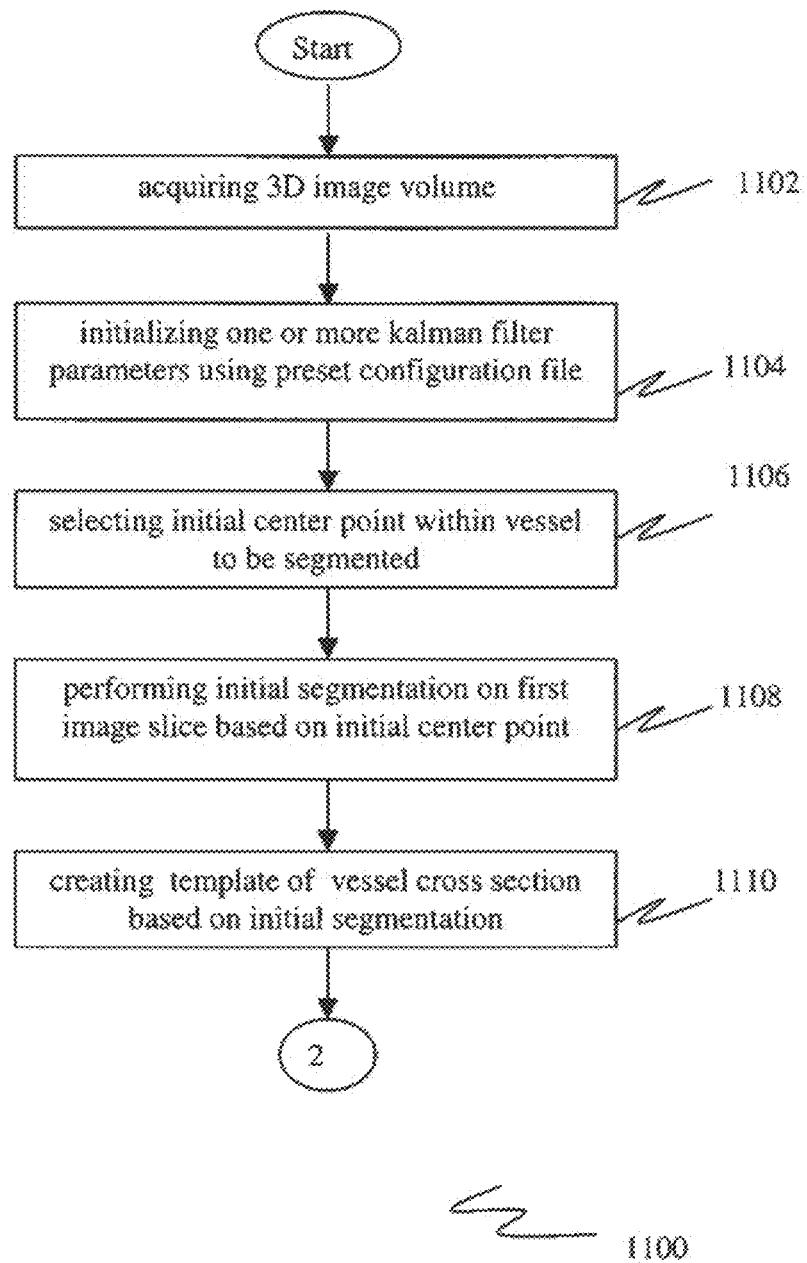
FIG. 11A and FIG. 11B show a flow chart that describes a method of segmenting a vessel comprising plurality of cross sections described in another embodiment.
Figure 11B:
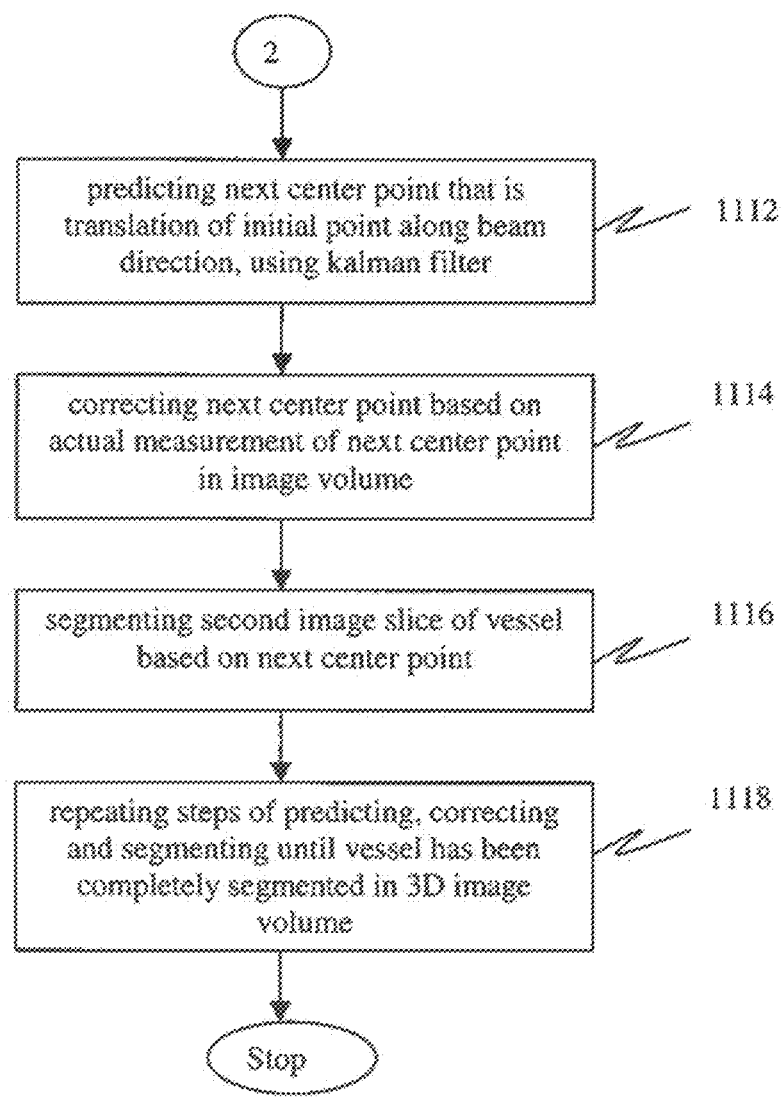

In yet another embodiment shown in FIG. 11A and FIG. 11B, a method 1100 for segmenting a vessel comprising plurality of cross sections is provided. The method 100 comprises steps of acquiring a 3D image volume at step 1102, initializing one or more Kalman filter parameters using a preset configuration file at step 1104, selecting an initial center point within the vessel to be segmented at step 1106, performing an initial segmentation on a first image shoe based on the initial center point, the first image slice being a 2D cross-section of the vessel, at step 1108, creating a template of a vessel cross section based on the initial segmentation at step 1110, predicting a next center point that is a translation of the initial point along a beam direction, using the Kalman filter, at step 1112, correcting the next center point based on a measurement of the next center point in the image volume at step 1114, segmenting a second image slice of the vessel, based on the next center point at step 1116 and repeating the steps of predicting, correcting and segmenting until the vessel has been completely segmented in the 3D image volume, at step 1118.

Steps 1102 to 1110 can be understood from the description provided above. Further, using the Kalman filter to predict a next center point, step 1112, comprises defining a transition matrix for translating the initial center point by a spatial displacement along the beam direction, defining a prediction error variance P for the initial center point, predicting a next center point and a next prediction error variance based on the transition matrix, defining process noise variance for the prediction error variance and the series of center point measurements, correcting the center point prediction based on a measurement error variance, a measurement of the predicted center point, and the process noise variance of the center point measurements, and correcting the prediction error variance based on the measurement error variance and the process noise variance of the center point measurements step 1114.

Subsequent to the step 1114, a second image slice of the vessel is obtained and segmented based on the corrected next center point at step 1116. The method 1100 further comprises repeating the steps of predicting, correcting and segmenting until the vessel has been completely segmented in the 3D image volume, at step 1118.

Thus, the initial segmentation of the first volume provides us with an extracted vessel centerline ($CL_0$), the centerline has to be maintained (i.e., tracked) over time (to get $CL_0$, $CL_1$, . . . , CL, etc). This is a challenging task because of numerous factors the time delay between two consecutive acquisitions ($\delta T_{aq}$), nominal probe motion, motion of the blood vessel under consideration due to cardiac pumping, breathing, etc. accordingly, the invention further describes a method of temporal centerline tracking.

Temporal tracking is an important part of vessel visualization, which enables maintaining and visualizing the centerline of a blood vessel over time. Temporal Kalman filter is used to track and maintain the vessel centerline in real-time over successively acquired 3D volumes. In practice, the blood vessels are segmented in cross-sectional ultrasound images in real-time, with frame rates of 10-16 Hz or more, and the feature location is tracked over successive 3D volumes using a temporal Kalman filter.

In order to perform this tracking, the initial segmentation of a vessel cross-section location is utilized to create a template of the cross-section and a Kalman filter based on template matching is used to track this cross-section through consecutive temporal volumes. The procedure of tracking images involves finding the relative movement between adjacent image frames in the sequence of intravascular ultrasound (IVUS) images, by calculating motion vectors, each of the motion vectors being the offset between adjacent image frames over a sparse grid of image rectangles.

Typically, there exists no large deviation in the vessel center location from one temporal slice to another and therefore the tracking parameters are initialized accordingly. For the Kalman filter dynamics, it is assumed that the vessel center moves with a constant velocity from tram to frame. The Kalman fiber has two distinct phases: predict and update. The predict phase uses the estimate from the previous time step to produce an estimate of the current state. In the update phase, measurement information from the current time step is used to refine this prediction to arrive at a new, more accurate estimate.

The method used for tracking the vessel centerline from one temporal volume to next is quite similar to the initial vessel centerline detection step in that a Kalman filter based tracking is performed and template matching is used for Kalman filter measurement step.

Though this approach is similar to the initial segmentation, an important difference is the template-matching measure used for cross-section tracking. A robust maximum-likelihood match measure is utilized that is derived by using the fact that the speckle in the cross-section image is approximated as a Rayleigh distribution.

Figure 12:
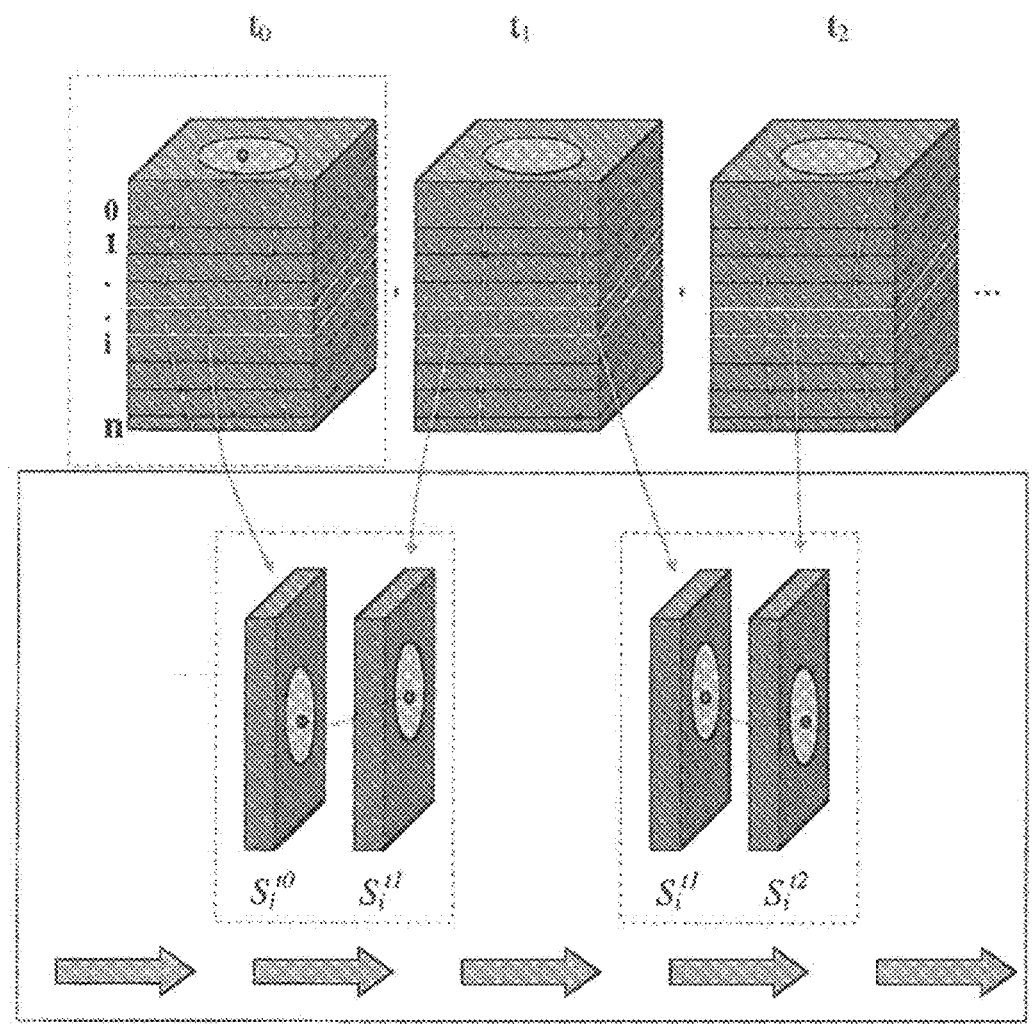
FIG. 12 shows a schematic diagram depicting an exemplary method tracking vessel cross-section in an imaging slice, as described in one embodiment.

FIG. 12 shows a schematic diagram depicting an exemplary method of tracking vessel-cross-section in an imaging slice-i. The temporal tracking for the "same" cross-sectional slice, i.e., $S_i^t$ is a temporally shifted image (at time t) of the "same" vessel cross-section slice $S_i^{t-1}$ in the previous time-slice (at time t-1). This allows the use of a similarity measure referred to herein as '$CD_2$ similarity measure'.

Using this similarity measure for template matching constraints the template update step (as a weighted template update cannot be performed, as the weighted template would not adhere to the Rayleigh approximation). Thus, the "newly-tracked" vessel cross-section is used as the update template. This is a special case of the weighted update where the weight given to the previous template is zero. This is efficient, as the $CD_2$ similarity measure has been shown to be robust for temporal matching.

It the process of tracking the vessel cross-section each cross-sectional slices are treated independent of each other (instead of a joint tracking method). To track the vessel as seen in say slice i ($S_i^t$), the center and vessel template from the slice i ($S_i^{t-1}$) in the previous temporal volume may be used. This initialization along with tracking parameters allows tracking the center point from $S_i^{t-1}$ to $S_i^t$. The steps shown in FIG. 1 are then carried out for each such slice-i, where i=0, 1, . . . , n.

Referring to the steps of selecting initial center and template described in the initialization step 104 of FIG. 1, for the first time slice after the initial segmentation (t1), the initial center and vessel-template is provided by the segmentation result (t0) given by the vessel center point estimated in the vessel segmentation step. For the succeeding time slice (t2), the initialization (center, template and tracking parameters) may be obtained from the tracking result for t1, and so on.

With continued reference to FIG. 1, referring to the step of setting up centerline tracking parameters described in the initialization step 104 of FIG. 1, the centerline tracking parameters can be described as comprising Kalman filter parameters and template matching parameters.

The Kalman filter parameters include process noise variance (Q) (set to be a constant, the sensitivity of tracking results to this parameter is low), measurement noise variance (R) (noise variance obtained from the image-based measurements i.e., the template matching score), estimate error variance (P) (computed by the Kalman Filter based on the measurement error and the system transition matrix (A), Kalman Gain (K) (updated at each step of the tracking), Delta_T (time-step, represents the number of time slices that are skipped, for tracking from one time point to next, this is set to be 1) and Lambda (parameter that is used to update, the measurement error variance).

Template matching parameters include initial observation window size (related to the actual vessel dimensions, and can be pre-computed using a default vessel size along with the acquisition geometry), match-score threshold (the template matching threshold used for determining if the measurement values are "coasting" and Alpha (parameter that controls total-match-score computation and facilitates biasing the template matching results in favor of the candidate that is closer to the prediction)

With reference to the Kalman filter initialization step 106 shown in FIG. 1, the Kalman filter parameters initialized using a preset configuration file. In subsequent time-steps, they get updated and are used for the subsequent time-steps. For example, for tracking the center point in slice-i of t1, initial parameters from the configuration/test file can be used.

However, at the end of this tracking step, the Kalman filter parameters are updated based on the measurement. These updated parameters are subsequently used for tracking the center point in slice-i of time-step t2, and so on.

With reference to the prediction step 108 shown in FIG. 1, the prediction step provides a predicted vessel center point based on the past observations. The Kalman filter utilizes the measurement error variance computed during the "Update" stage of the previous tracking step, in order to estimate the prediction (i.e., the contribution of the previous center point is more if the measurement error during the estimation of the previous center point was small).

With continued reference to FIG. 1, the step 110 of checking validity of Kalman prediction includes, checking if the predicted center point ($C_{kp}$) is within the volume bounds, and also that the estimation error is reasonable.

With reference to the Kalman filter based template-matching step 112 shown in FIG. 1, the similarity between the estimated template and the measured template is computed using the $CD_2$ similarity measure. This similarity considers a maximum likelihood computation that utilizes the approximate Rayleigh distribution of the speckle noise.

The $CD_2$ similarity measure is especially useful when two temporally separated slices/volumes of ultrasound data are being compared, which (approximately) correspond to the same physical location in the subject. If $A=[A_{ij}]$ are the pixels of the vessel cross-section in $S_i^{t-1}$ and $B=[B_{ij}]$ are the pixels of the same vessel cross-section in $S_i^t$, then the multiplicative Rayleigh-noise approximation is used to compute the matchscore for A and B using maximum likelihood and treating individual pixels independent of each other.

With reference to the subsequent Kalman filter updating step 114 shown in FIG. 1, the Measured Center point ($C_{km}$) and Velocity ($V_{km}$) along with Measurement error variance ($R_k$) obtained from using CD2 measure are fed as inputs to obtain the next vessel center point.

The first task during the measurement update to compute the Kalman gain. The next step is to actually measure the process, and then to generate a posteriori estimate by incorporating the measurement. The final step is to obtain a posteriori error variance estimate. The Kalman gain (K) thus obtained is updated thereafter for use in the future iterations.

The steps of predicting the vessel center point step 108, checking validity of prediction step 110, performing template matching to estimate measurement error step 112 and subsequent updating of the Kalman filter step 114 are repeated for each slice-i, (shown in FIG. 12), where i=0, 1, . . . , n.

Figure 13:
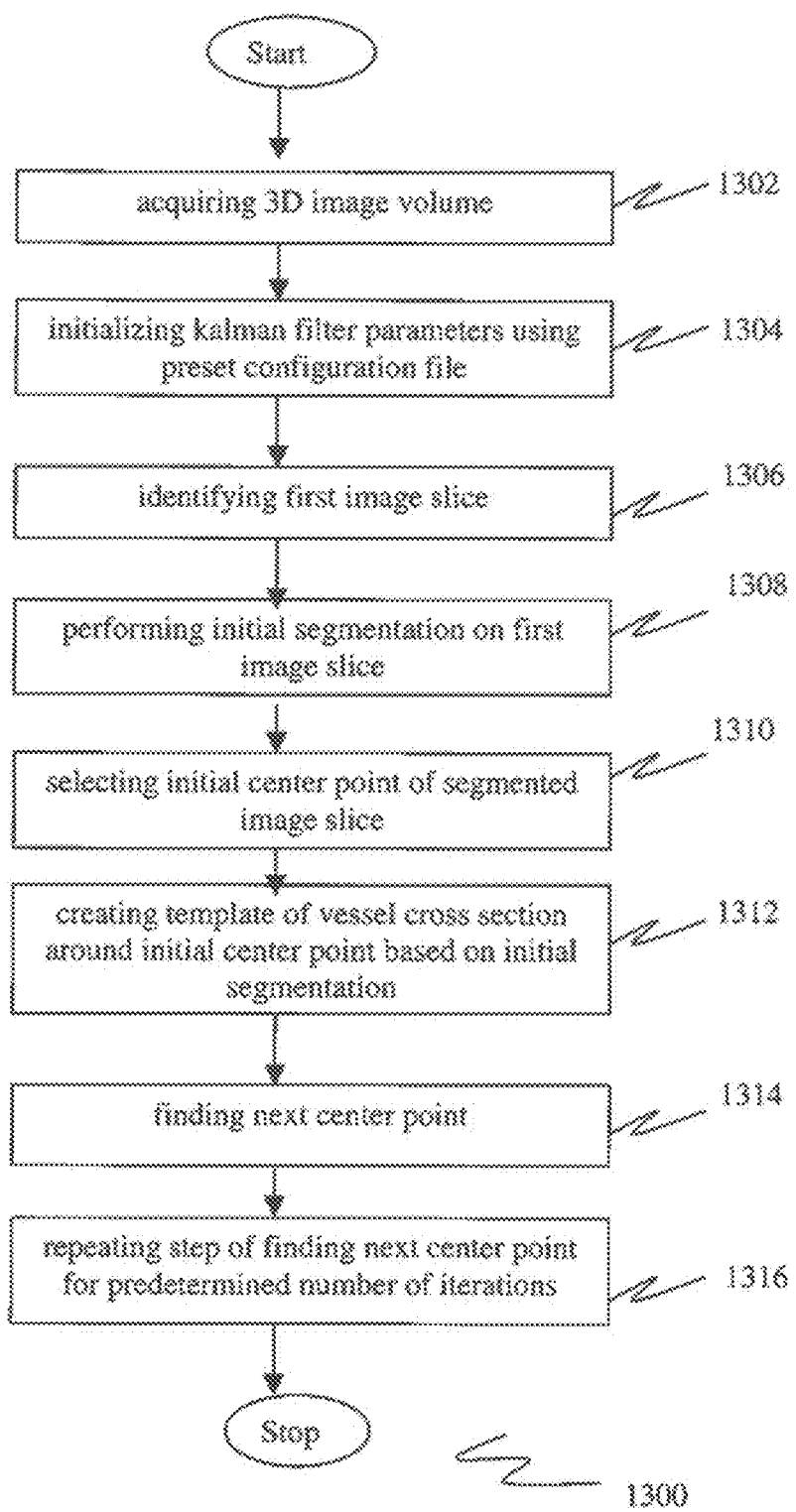
FIG. 13 shows a flow chart that describes a method of vessel temporal tracking as described in one embodiment.

FIG. 13 shows a flowchart describing an overview of the temporal centerline-tracking method 1300 implemented for each image slice along the vessel, as described in another embodiment. The method of vessel temporal tracking 1300 comprises steps of acquiring a 3D image volume at step 1302, initializing the Kalman fiber parameters using the preset configuration file at step 1304, identifying a first image slice at step 1306, performing an initial segmentation on the firs image slice at step 1308, selecting an initial center point of the segmented image slice at step 1310, creating a template of the vessel cross section around the initial center point based on the initial segmentation, at step 1312, finding a next center point at step 1314 and repeating the step of finding the next center point until an end point of the vessel centerline is reached or for a predetermined number of iterations, at step 1316.

Figure 14:
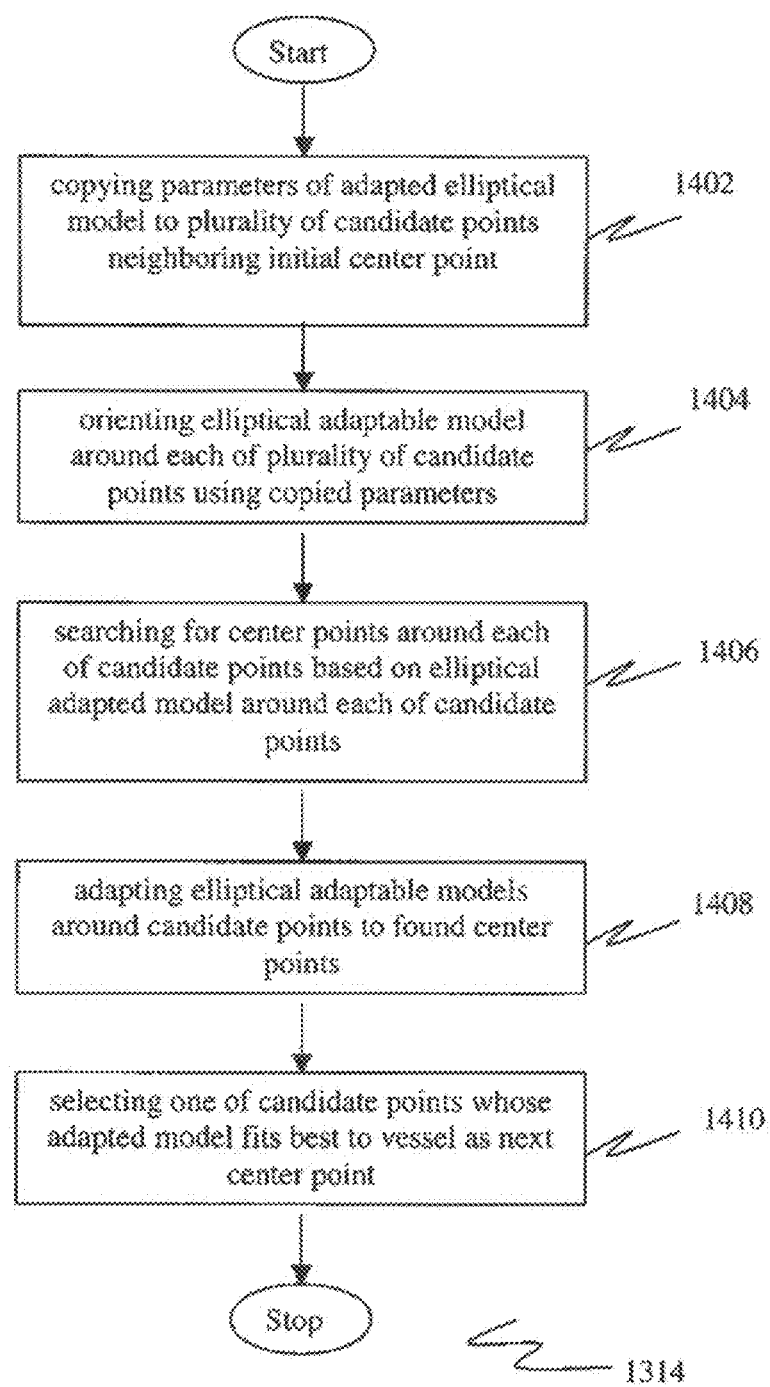
FIG. 14 shows a flow chart that describes the step of finding a next center point shown FIG. 13.

As described in one embodiment listed above, the template of the vessel cross-section is approximated to be an ellipse. Accordingly, an adaptive elliptical model is employed in finding the next center point. Step 1314 of finding the next center point is further explained in conjunction with FIG. 14. With reference to FIG. 14, step 1314 comprises steps of copying parameters of the adapted elliptical model to a plurality of candidate points neighboring the initial center point at step 1402, orienting an elliptical adaptable model around each of the plurality of candidate points using the copied parameters at step 1404, searching for center points around each of the candidate points based on the elliptical adapted model around each of the candidate points at step 1406, adapting the elliptical adaptable models around the candidate points to the found center points at step 1408 and selecting one of the candidate points whose adapted model fits best to the vessel as the next center point at step 1410.

Step 1406 of searching for center points around each of the candidate points comprises performing morphological filtering to eliminate structures smaller than a speckle size. Further, performing morphological filtering includes steps of counting the number of continuous vessels in the search region, computing the area of each continuous vessels and rejecting vessels having an area lying outside a predetermined range.

In general, a target search region may contain more than one vessel segment. The "best" vessel segment can be chosen based on any reasonable morphological characteristic, such as the vessel diameter (closest to a standard size of the vessel type associated with the user-selected application type), greatest vessel length or area, or most uniform diameter (since the user usually moves the probe to obtain the best view of the vessel of interest), or a combination of goodness measures. Alternatively, the best vessel segment can be defined as the one, which is at the shortest distance from the preset position.

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to and executed by, a machine comprising any suitable architecture.

Accordingly, in yet another embodiment, a computer system comprising: a processor and a program storage device readable by the computer system, embodying a program of instructions executable by the processor to perform method steps for automatic segmentation and temporal tracking of a blood vessel is provided. The method comprises steps of acquiring an image volume from an ultrasound imaging system, performing vessel segmentation on the 3D image volume to generate a 3D ultrasound image of the blood vessel, detecting a vessel centerline for the segmented blood vessel, estimating cross-sectional area of the segmented blood vessel using the calculated vessel centerline and performing temporal tracking of the estimated cross-section based on a template matching criteria. Each of the steps is described in methods illustrated in the above embodiments. The step of detecting a vessel centerline is described in method 100. The step of estimating the cross-sectional area of the segmented vessel is described in method 700 and the step of performing temporal tracking is described in method 1300.

A technical effect of one or more embodiments of the invention described herein includes automated segmentation and tracking of three-dimensional anatomical data formed from combinations of datasets, using a single software tool, for purposes of efficient diagnosis.

Another technical effect of the methods disclosed herein includes providing information and images for planning and conducting interventional procedures, thereby enabling a electrophysiologist, cardiologist, and/or surgeon to efficiently conduct the interventional procedure.

The feasibility of the methods described herein namely, the vessel centerline detection, segmentation and temporal tracking has been demonstrated using a synthetic (simulated static vessel phantom) and an in-vivo 3D datasets both of which do not contain any catheters.

The methods for vessel segmentation and tracking described herein provide an improved visualization capability to view all the vascular elements inside an acquisition volume procured using ultrasound imaging. The methods described herein aid the clinician by highlighting a vascular tree of interest that helps the clinician distinguish the vascular tree from other surrounding anatomy. Further, the methods allow the visualization of desired vessels even during the presence of motion.

Also, the methods described herein provide an improved visualization of the catheter. This helps a clinician in guiding a needle or catheter to a desired location while avoiding potential damage to the surrounding tissue. The segmented vessels not only ease the clinician's difficulty to correctly and precisely place and advance the catheter under the guidance of ultrasound, but also pave the way toward building more clinically meaningful views of the catheter in the real-time 3D data, such as the vessel center-line curved cut views.

When the methods of vessel segmentation and tracking described herein are used in diagnostic ultrasound imaging, the capability of the methods to provide automatic segmentation and improved visualization results in decreasing the amount of training required to use the ultrasound imaging system.

Further, the methods described herein are automatic, that may be adapted to select the best viewing planes (or volumes) for display, eliminating the need for complicated user interface.

The invention describes methods using a Kalman filter for centerline detection, segmentation and temporal tracking. Because the Kalman filter is designed to operate in the presence of noise, an approximate fit is often good enough for the filter to be very useful. Thus, though, in general, ultrasound images suffer from heavy speckle noise, the methods described herein can be more efficient in providing improved vessel visualization.

In various embodiments of the invention, segmentation and tracking methods for an ultrasound imaging system and an ultrasound imaging system using the segmentation and tracking methods am described. However, the embodiments are not limited and may be implemented in connection with different applications. The application of the invention can be extended to other areas, for example other imaging devices. Specific clinical application areas include echocardiography, breast ultrasound, transrectal ultrasound (TRUS), and intravascular ultrasound (IVUS)] and multiple methods that use assumed feature geometry. The invention provides a broad concept of using segmentation and tracking methods to improve visualization, which can be adapted in any imaging system used for non-medical applications. The design can be carried further and implemented in various forms and specifications.

This written description uses examples to describe the subject matter herein, including the best mode, and also to enable any person skilled in the art to make and use the subject matter. The patentable scope of the subject matter is defined by the claims, and may include other examples that occur to those skilled in the art. Such other examples are intended to be within the scope of the claims if they have structural elements that do no differ from the literal language of the claims, or if they include equivalent structural elements with insubstantial differences from the literal language of the claims.

What is claimed is:

1. A method of vessel temporal tracking, the method comprising:
    acquiring a 3D image volume;
    initializing one or more Kalman filter parameters using a preset configuration file;
    identifying a first image slice;
    performing an initial segmentation on the first image slice;
    selecting an initial center point of the segmented image slice;
    creating a template of a vessel cross section around the initial center point based on the initial segmentation, the template being an elliptical model;
    predicting a next center point using the one or more Kalman filters;
    finding a next center point by the steps of: copying parameters of the adapted elliptical model to a plurality of candidate points neighboring the initial center point; orienting an elliptical adaptable model around each of the plurality of candidate points using the copied parameters; searching for center points around each of the candidate points based on the elliptical adapted model around each of the candidate points; adapting the elliptical adaptable models around the candidate points to the found center points; selecting one of the candidate points whose adapted model fits best to the vessel as the next center point, updating a centerline based on the predicted or selected center point, and repeating the steps of predicting or finding a next center point until an end point of the vessel centerline or a predetermined number of iterations are reached.

2. The method of claim 1, wherein the similarity is computed using CD2 similarity measure.

3. The method of claim 1, wherein the searching step comprises performing morphological filtering to eliminate structures smaller than a speckle size.

4. The method of claim 3, wherein the searching step further comprises:
    counting the number of continuous vessels in the search region;
    computing the area of each continuous vessels; and
    rejecting vessels having an area lying outside a predetermined range.

5. A computer system comprising: a processor and a program storage device readable by the computer system, embodying a program of instructions executable by the processor to perform method steps for automatic segmentation and temporal tracking of a blood vessel in a 2D or 3D image data set by extracting a centerline along the blood vessel in a selected region, the method comprising:
    acquiring an image volume from an ultrasound imaging system;
    performing vessel segmentation on the 3D image volume to generate a 3D ultrasound image of the blood vessel;
    detecting a vessel centerline for the segmented blood vessel, where detecting the vessel centerline includes:
    initializing a centerline;
    initializing a Kalman filter;
    predicting a next center point using the Kalman filter;
    checking validity of the prediction;
    updating the vessel centerline based on the predicted next centerpoint;
    performing template matching for estimating measurement error;

updating the Kalman filter based on the template matching; and repeating the steps of predicting, checking, performing and updating for a predetermined number of times, estimating cross-sectional area of the segmented blood vessel using the calculated vessel centerline; and performing temporal tracking of the estimated cross-section based on template matching.

6. The method of claim 5, wherein the method of estimating cross-sectional area comprises steps of:

initializing a vessel cross section;

initializing an iteration counter;

evolving an active contour towards a vessel boundary;

regularizing a contour from the active contour evolution by using least square fitting;

determining if the value of the iteration counter is greater than a predetermined value;

performing the initialization using the regularized contour if the value of the iteration counter is less than the predetermined value;

incrementing the iteration counter; and repeating the steps of evolving, regularizing, determining, performing and incrementing for a predetermined number of iterations indicated by the predetermined value.

7. The computer system of claim 5, wherein the method of performing temporal tracking comprises steps of:

initializing one or more Kalman filter parameters using a preset configuration file:

identifying a first image slice;

performing an initial segmentation on the first image slice;

selecting an initial center point of the segmented image slice;

creating a template of a vessel cross section around the initial center point based on the initial segmentation, the template being an elliptical model;

finding a next center point by the steps of: copying parameters of the adapted elliptical model to a plurality of candidate points neighboring the initial center point;

orienting an elliptical adaptable model around each of the plurality of candidate points using the copied parameters; searching for center points around each of the candidate points based on the elliptical adapted model around each of the candidate points; adapting the elliptical adaptable models around the candidate points to the found center points; selecting one of the candidate points whose adapted model fits best to the vessel as the next center point and repeating the step of finding a next center point until an end point of the vessel centerline or a predetermined number of iterations are reached.

* * * * *